United States Patent [19]

Merrifield

[11] Patent Number: 4,879,273
[45] Date of Patent: Nov. 7, 1989

[54] GLUCAGON HOMOLOGS AND THERAPEUTIC USE THEREOF

[75] Inventor: Robert B. Merrifield, Cresskill, N.J.

[73] Assignee: The Rockefeller University, New York, N.Y.

[21] Appl. No.: 53,407

[22] Filed: May 22, 1987

[51] Int. Cl.[4] .................. A61K 37/28; C07K 7/10; C07K 7/34

[52] U.S. Cl. .................. 514/12; 530/308; 530/324

[58] Field of Search .............. 530/308, 324; 514/12

[56] References Cited

U.S. PATENT DOCUMENTS 3,642,763  2/1972  Wunsch et al. ............... 530/308
4,423,034 12/1983  Nakagawa et al. ............ 530/308

OTHER PUBLICATIONS

Rudinger, Peptide Hormones, Parsons (ed.), U. Park Press, Baltimore, pp. 1–7 (1976).

Primary Examiner—Delbert R. Phillips
Assistant Examiner—Christina Chan
Attorney, Agent, or Firm—Wyatt, Gerber, Burke and Badie

[57] ABSTRACT

Glucagon analogs characterized principally by deletion of the number one histidine and replacement of the number nine aspartic acid with glutamic acid are useful adjuncts to insulin therapy.

16 Claims, No Drawings

GLUCAGON HOMOLOGS AND THERAPEUTIC USE THEREOF

BACKGROUND OF THE INVENTION

Glucagon is a 29-residue peptide hormone that regulates glucogenolysis and gluconegenesis. The structure of glucagon may be represented as follows:

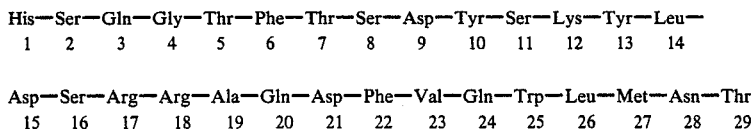

The abbreviations utilized herein are those recommended by IUPAC-IUB [see Eur. J. Biochem. 138, 9 (1984)].

Insulin, as is known, rapidly decreases elevated blood sugar.

It is believed that in humans diabetes is only observed when insulin levels are low and glucagon is elevated. The absence of insulin allows blood glucose to rise particularly after a meal, and the presence of glucagon causes a further rise in blood glucose. Large amounts of insulin are required to reduce the glucose levels to normal. The maintenance of stable levels is difficult and subject to considerable fluctuation. This wide fluctuation is responsible, at least in part, for the clinical difficulties experienced in diabetes.

Glucagon appears to act by binding to the liver membrane thereby activating adenylate cyclase which, in turn, triggers a series of reactions including the production of cyclic adenosine monophosphate (cAMP) which activates phosphorylase and inhibit glycogen synthetase, thereby contributing to elevated glucose levels in the blood.

Recently considerable effort has been expended to develop glucagon antagonists which will bind to the liver membrane but do not have the ability to tranduce the signal to activate adenylate cyclase. One such product is N$\alpha$- trinitrophenyl [12-homoarginine] glucagon. This product does bind to the glucagon receptor without significant activation of adenylate cyclase. Unfortunately it activates another binding system in the hepatocyte membrane leading to the production of inositol triphosphate and calcium ions. A useful antagonist will block the action of endogenous glucagon by preventing it from binding to the liver membrane receptors and thereby producing cAMP and glucose in the cell, and the ultimate elevation of blood sugar. Such products would be useful to reduce a diabetics need for injections or infusion of insulin.

An ideal glucagon antagonist would (1) be completely inactive toward stimulation of adenylate cyclase and production of cAMP, (2) bind as well as glucagon itself to the liver membrane, (3) compete with glucagon for binding to the membrane, (4) at moderate concentrations fully inhibit the action of glucagon toward the activation of adenylate cyclase, and (5) have a satisfactory inhibition index.

The inhibition index is the molar ratio of antagonist to agonist which reduces the biological response to one half of the value for the agonist in the absence of antagonists. It will be discussed more fully hereinafter.

THE INVENTION

A class of glucagon antagonists has now been discovered which substantially fulfills the above criteria and does so with minimum side effects. Unexpectedly, the members of the class also appear to stimulate the release of insulin from the B-cells of the pancreatic islets, thus further minimizing the need for therapeutically administered insulin.

The compounds of this invention are best visualized as analogs of glucagon in which the number one histidine moiety has been removed and the number nine aspartic acid has been replaced with glutamic acid. A much preferred subgenus of the class has the same distinguishing characteristics and, in addition, the terminal carboxyl group on the threonine is converted to an amide. The compounds may be represented by the notation:

des-His$^1$-[Glu$^9$] glucagon, and des-His$^1$-[Glu$^9$] glucagon amide.

Other amino acids in the glucagon chain may be replaced to produce useful compounds, but the removal of the amino terminal histidine and the replacement of the number nine aspartic acid with glutamic acid appear to make the principal contributions to the utility of the final compounds. Such compounds as:

des-His$^1$-[Glu$^9$-Lys$^{17,18}$Glu$^{21}$] glucagon and the corresponding amide have somewhat lesser membrane binding activity but are essentially inactive in adenylate cyclase assays.

The products of this invention were synthesized by known solid phase techniques. See, for example, Barany and Merrifield (1979) in *The Peptides*, eds. Gross and Meienhofer (Academic Press, New York) Vol. 2A, pages 1 to 284. The products can be prepared by manual methods or, for example, on a peptide synthesizer such as the Applied Biosystems 430 unit.

Analogs with a free C-terminal carboxyl were made on phenylacetamidomethyl-resin supports, and those with C-terminal amides were made on a methylbenzhydrylamine-resin. Side chain protection was Arg(Tos), Asp(OcHx), Glu(OcHx), His(Tos), Lys(ClZ), Ser(Bzl), Thr(Bzl), Trp(For), and Tyr(BrZ). Double couplings with preformed symmetric anhydrides in dimethylformamide were used routinely for all tert-butyloxycarbonyl-protected amino acids except for tosyl arginine, glutamine, and asparagine, where esters in dimethylformamide were required [Konig, W. & Geiger, R. Chem. Ber. 103, 788 (1970)]. The assembled protected peptide-resins were cleaved by the "low/high HF" technique [Tam, J. P., Heath, W. F. & Merrifield, R. B. J. Am. Chem. Soc. 105, 6442 (1983)], which was developed to avoid a number of potential side reactions. After evaporation of HF and washing with ether, the crude free peptide was extracted with 10% acetic acid and lyophilized. Purification of the synthetic peptides was performed by preparative low-pressure reverse-phase liquid chromatography on $C_{18}$-silica as described [Andreu, D. & Merrifield, R. B. in Peptides: Structure and Function, eds. Deber, C. M., Hruby, V. J. & Kopple, K. D. (Pierce Chem. Co., Rockford, Ill.), pp. 595–598. The overall yields were between 35 and 40%. Homogeneity was demonstrated by analytical HPLC, and identity was confirmed by amino acid analysis.

The amino acid analysis of all compounds prepared agreed with theory within ±5%.

Tert-Butyloxycarbonyl (Boc) protected amino acids were from Peninsula Laboratories, (San Carlos, (A.) p-methylbenzhydrylamine resin (0.45 mmol/g) was from United States Biochemical (Cleveland, Ohio) and Boc-Thr-(Bzl)-4-oxymethylphenylacetamidomethyl copoly (styrene-1% divinyl benzene) was prepared as described by Mitchell et al, J. Org. Chem. 43, 2845 (1978).

$^{125}$I-labeled glucagon from New England Nuclear was used without further purification for periods up to 1 month after its preparation. Creatine phosphate, creatine kinase, bovine serum albumin, dithiothreitol, GTP, and ATP were from Sigma. A cAMP assay kit containing [8-$^3$H]cAMP was from Amersham. Nuflow membrane filters (0.45 um) were from Oxoid (Basingstoke, England).

Various tests were employed to determine the efficacy of the products of this invention. These included the membrane binding assay and adenyl cyclase assays.

Membrane Binding Assay. Liver plasma membranes were prepared from male Sprague-Dawley rats (Charles River Breeding Laboratories) by the Neville procedure as described by Pohl [Pohl, S. L. (1976) in Methods in Receptor Research, ed. Blecher, M. (Marcel Dekker, New York), pp. 160–164]. The receptor binding assay was as described by Wright and Rodbell [Wright, D. E. & Rodbell, M. (1979) J. Biol. Chem. 254, 268–269] in which competition for glucagon receptors between $^{125}$I-labeled natural glucagon (1.6 nM) and the unlabeled synthetic analog was measured. After correction for the blank, the percentage of displacement of label was compared with that of a purified glucagon standard, and the relative binding affinity was calculated.

Adenylate Cyclase Assay. The assay on liver membranes was performed according to Salomon et al. [Salomon, Y., Londos, C. & Rodbell, M. Anal. Biochem. 58, 541,548 (1974)]. The released cAMP was mixed with [8-$^3$H]cAMP measured with a high affinity cAMP binding protein.

The purpose of the membrane binding assay is to measure the ability of analogs of glucagon to bind to liver plasma protein compared to that of glucagon.

When glucagon analogs are assayed, natural glucagon is assayed as a standard simultaneously, thus eliminating the possibility of imprecision due to the heterogeneity of membrane preparations. The relative binding affinity of a given analog is expressed as:

$$\frac{\text{(half maximal displacement concentration of glucagon)}}{\text{(half maximal displacement concentration of analog)}} \times 100$$

The purpose of the adenylate cyclase assays is to measure the ability of the compound under test to stimulate the activity of adenylate cyclase. The assays are used to measure relative potency, maximum activity and inhibition index.

The inhibition index, defined above, was determined from adenylate cyclase assays by two different protocols.

1. A glucagon standard curve for cAMP vs glucagon concentration was established. Then another glucagon assay curve was measured in the presence of a constant amount of antagonist. The concentration of glucagon which had its activity reduced to 50% by that concentration of inhibitor was then determined.

2. A series of tubes were set up containing an amount of glucagon which will produce 90% of maximum response. Increasing amounts of antagonist were then added and the concentration that reduced the response to 45% of maximum was determined.

Since normal circulating levels of glucagon are about $10^{10}$ molar, a product with an inhibition index of 12 would only need to be present in vivo at a concentration of 0.4 μg/ml of blood to inhibit completely the action of glucagon. The compounds of this invention have an inhibition index up to about 35, but preferably up to 15, coupled with a membrane binding activity of at least 10%. It is much preferred that the inhibition index be 12 or less.

The following Table shows the results of measurements with glucagon and certain of the compounds of this invention.

| | COMPETITIVE INHIBITION OF GLUCAGON BY SYNTHETIC ANALOGS | | | | | | | |
|---|---|---|---|---|---|---|---|---|
| | TYPE OF REPLACEMENT | | | | MEMBRANE BINDING | ADENYL CYCLASE ASSAYS | | |
| # | Delete | Analog | Added | Amide | Relative % | Max. Act. % | Rel. Potency | Inhib. Index |
| A | | GLUCAGON | | | 100 | 100 | 100 | |
| 1 | des His$^1$ | Glu$^9$ | | | 11 | 0 | <0.0008 | 36 |
| 2 | des His$^1$ | Glu$^9$ | | NH$_2$ | 41 | 0 | <0.0001 | 12 |
| 3 | des His$^1$ | Glu$^9$ | Lys$^{17,18}$Glu$^{21}$ | | 10 | 0 | 0.0001 | 12.6 |

It will be noted that the compound of the second row, which is an amide, has a much higher membrane binding activity than the corresponding carboxyl compound.

The products of this invention will generally be administered in the same manner as insulin, i.e. parenterally or by infusion. Since their chemical structure and activity is quite similar to insulin they will generally be administered with the same types of pharmaceutically acceptable excipients as insulin. They may in fact be coadministered with insulin in the same dosage units. They may also be administered simultaneously with the insulin although not in the same composition.

Since the products of the invention are amphoteric they may be utilized as free bases, as acid addition salts or as metal salts. The salts must, of course, be pharmaceutically acceptable, and these will include metal salts particularly alkali and alkaline earth metal salts, suitably potassium or sodium salts. A wide variety of pharmaceutically acceptable acid addition salts are available.

These include those prepared from both organic and inorganic acids, preferably mineral acids. Typical acids which may be mentioned by way of example include citric, succinic, lactic, hydrochloric and hydrobromic acids. Such products are readily prepared by procedures well known to those skilled in the art.

The products of the invention will normally be provided for as parenteral compositions for injection or infusion. They can, for example be suspended in an inert oil, suitably a vegetable oil such as sesame, peanut, or olive oil. Alternatively they can be suspended in an aqueous isotonic buffer solution at a pH of about 5.6 to 7.4. Useful buffers include sodium citrate-citric acid and sodium phosphate-phosphoric acid.

The desired isotonicity may be accomplished using sodium chloride or other pharmaceutically acceptable agents such as dextrose, boric acid, sodium tartrate, propylene glycol or other inorganic or organic solutes. Sodium chloride is preferred particularly for buffers containing sodium ions.

If desired the solutions may be thickened with a thickening agent such as methyl cellulose. They may be prepared in emulsified form, either water in oil or oil in water. Any of a wide variety of pharmaceutically acceptable emulsifying agents may be employed including, for example acacia powder, or an alkaryl polyether alcohol sulfate or sulfonate such as a Triton.

The therapeutically useful compositions of the invention are prepared by mixing the ingredients following generally accepted procedures. For example, the selected components may be simply mixed in a blender or other standard device to produce a concentrated mixture which may then be adjusted to the final concentration and viscosity by the addition of water or thickening agent and possibly a buffer to control pH or an additional solute to control tonicity.

For use by the physician, the compositions will be provided in dosage unit form containing an amount of glucagon analog which will be effective in one or multiple doses to control glucogenesis or blood sugar at the selected level, normally in the presence of insulin. As will be recognized by those skilled in the art, an effective amount of the therapeutic agent will vary with many factors including the age and weight of the patient, the amount of insulin which is concurrently employed, the blood sugar level to be obtained, the inhibition index of the selected analog, and other factors. Typical dosage units will contain from 0.2 to 0.8 µg/ml although wide variations from this range are possible while yet achieving useful results.

What is claimed is:

1. des-His$^1$-[Glu$^9$] glucagon.
2. des-His$^1$-[Glu$^9$] glucagon amide.
3. des-His$^1$-[Glu$^9$Lys$^{17,18}$-Glu$^{21}$] glucagon.
4. A pharmaceutically acceptable metal or acid addition salt of a compound of claims 1, 2, or 3.
5. A parenteral composition for the control of glucogenesis in humans containing a pharmaceutically acceptable carrier and an amount of des-His$^1$-[Glu$^9$] glucagon which is sufficient to effect such control.
6. A parenteral composition for the control of glucogenesis in humans containing a pharmaceutically acceptable carrier and an amount of des-His$^1$-[Glu$^9$] glucagon amide which is sufficient to effect such control.
7. A parenteral composition for the control of glucogenesis in humans containing a pharmaceutically acceptable carrier and an amount of a pharmaceutically acceptable metal or acid addition salt of des-His$^1$-[Glu$^9$] glucagon which is sufficient to effect such control.
8. A parenteral composition for the control of glucogenesis in humans containing a pharmaceutically acceptable carrier and an amount of a pharmaceutically acceptable metal or acid addition salt of des-His$^1$-[Glu$^9$] glucagon amide which is sufficient to effect such control.
9. A parenteral composition in dosage unit form for the control of glucogenesis in humans containing a pharmaceutically acceptable carrier and from about 0.2 to 0.8 µg/ml of des-His$^1$-[Glu$^9$] glucagon.
10. A parenteral composition in dosage unit form for the control of glucogenesis in humans containing a pharmaceutically acceptable carrier and from about 0.2 to 0.8 µg/ml of des-His$^1$-[Glu$^9$] glucagon amide.
11. A parenteral composition in dosage unit form for the control of glucogenesis in humans containing a pharmaceutically acceptable carrier and from about 0.2 to 0.8 µg/ml of a metal or acid addition salt of des-His$^1$-[Glu$^9$] glucagon.
12. A parenteral composition in dosage unit form for the control of glucogenesis in humans containing a pharmaceutically acceptable carrier and from about 0.2 to 0.8 µg/ml of a metal or acid addition salt of des-His$^1$-[Glu$^9$] glucagon amide.
13. A parenteral composition for the control of glucogenesis in humans containing a pharmaceutically acceptable carrier and an amount of des-His$^1$-[Glu$^9$-Lys$^{17,18}$-Glu$^{21}$] glucagon which is sufficient to effect such control.
14. A parenteral composition for the control of glucogenesis in humans containing a pharmaceutically acceptable carrier and an amount of a pharmaceutically acceptable metal or acid addition salt of des-His$^1$-[Glu$^9$-Lys$^{17,18}$-Glu$^{21}$] glucagon which is sufficient to effect such control.
15. A parenteral composition in dosage unit form for the control of glucogenesis in humans containing a pharmaceutically acceptable carrier and from about 0.2 to 0.8 µg/ml of des-His$^1$-[Glu$^9$-Lys$^{17,18}$-Glu$^{21}$] glucagon.
16. A parenteral composition in dosage unit form for the control of glucogenesis in humans containing a pharmaceutically acceptable carrier and from about 0.2 to 0.8 µg/ml of a metal or acid addition salt of des-His$^1$-[Glu$^9$-Lys$^{17,18}$-Glu$^{21}$] glucagon.

* * * * *